United States Patent [19]

Hosokawa et al.

[11] Patent Number: 4,542,143
[45] Date of Patent: Sep. 17, 1985

[54] PYRIDYL CARBONYL ASCOCHLORIN DERIVATIVES AND PHARMACEUTICAL COMPOSITIONS CONTAINING THE SAME

[75] Inventors: Tomoyoshi Hosokawa, Kanagawa; Ikutoshi Matsuura; Hidenori Takahashi, both of Saitama; Kunio Ando, Kanagawa; Gakuzo Tamura, Tokyo, all of Japan

[73] Assignee: Chugai Seiyaku Kabushiki Kaisha, Tokyo, Japan

[21] Appl. No.: 607,400

[22] Filed: May 3, 1984

Related U.S. Application Data

[62] Division of Ser. No. 412,075, Aug. 27, 1982, Pat. No. 4,500,544.

[30] Foreign Application Priority Data

Sep. 10, 1981 [JP] Japan ................... 56-141660
Oct. 23, 1981 [JP] Japan ................... 56-168821

[51] Int. Cl.$^4$ ............... C07D 213/79; C07D 213/80; A61K 31/455
[52] U.S. Cl. ........................... 514/356; 514/354; 546/322; 546/326
[58] Field of Search ............... 546/322, 326; 424/266

[56] References Cited

U.S. PATENT DOCUMENTS

3,546,073 12/1970 Evans et al. .................. 195/81
3,995,061 11/1976 Hosokawa et al. ............ 424/331

OTHER PUBLICATIONS

Chem. Abstracts, vol. 94:96316x.
Chem. Abstracts, vol. 86:34279p.
Sherif, E. A. et al., "Synthesis of Chalcones, Flavanones Isolated from Popowia Cauliflora and their Analogs", Agric. Biol. Chem., vol. 45(2), 531–533, (1981).

Primary Examiner—Henry R. Jiles
Assistant Examiner—Dale A. Bjorkman
Attorney, Agent, or Firm—Browdy and Neimark

[57] ABSTRACT

Ascochlorin derivatives of the formula:

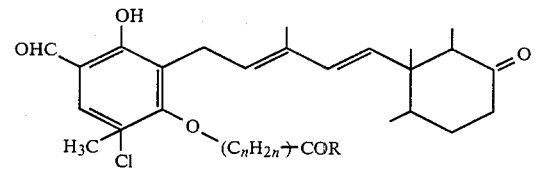

wherein R is a hydroxyl group, a lower alkoxy group, a pyridyl group, an amino group, a dialkylamino group, a phenoxyalkyl group which may have a substituent in the nucleus, or a phenyl group which may have a substituent in the nucleus; and n is an integer of 0 to 5, a process for preparing the same and a pharmaceutical composition containing the same are disclosed.

The derivatives are useful to treat diabetes, improve lipid metabolism and control tumors.

15 Claims, No Drawings

PYRIDYL CARBONYL ASCOCHLORIN DERIVATIVES AND PHARMACEUTICAL COMPOSITIONS CONTAINING THE SAME

This is a division, of application Ser. No. 412,075 filed Aug. 27, 1982, U.S. Pat. No. 4,500,544.

The present invention relates to novel ascochlorin derivatives. Ascochlorin is an antibiotic that was found in the culture broth of a mold *Ascochyta viciae* by the present inventors (reference should be had to Japanese Pat. No. 585,252). It has high anti-viral and anti-tumor effects, but since it is also highly toxic to the circulatory system of mammals, studies have been made on the pharmaceutical use of a compound prepared by methylating the hydroxyl group at a 4-position of orcylaldehyde (Agr. Biol. Chem., 45, 531). But this compound is low in water solubility and its level in blood is not easily increased even if it is administered systemically or orally.

The present inventors have made various studies to create ascochlorin derivatives that are free from the defects of the conventional compound and which yet retains the good pharmacological effects of ascochlorin, and have unexpectedly found that derivatives prepared by reacting ascochlorin with straight or branched lower aliphatic acids having a halogen atom or esters thereof enhance the peripheral insulin sensitivity, improve the lipid and carbohydrate metabolism and prevent the growth of experimental tumors.

The present invention relates to a process for producing these ascochlorin derivatives that have the general formula:

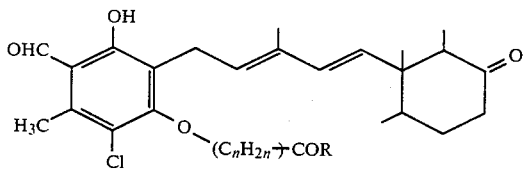

(I)

(wherein R is a hydroxyl group, a lower alkoxy group preferably having carbon atoms of from 1 to 6, a pyridyl group, an amino group, a dialkylamino group preferably having carbon atoms of from 2 to 8, a phenoxyalkyl group which may have a substituent in the nucleus or a phenyl group which may have a substituent in the nucleus; n is an integer of 0 to 5).

Examples of the substituent of the phenoxyalkyl group in the formula (I) are a halogen atom, an alkyl group, preferably having carbon atoms of from 1 to 4, and an alkoxy group having carbon atoms of from 1 to 4. Examples of the substituent of the phenyl group in the formula (I) are a halogen atom, an alkyl group, preferably having carbon atoms of from 1 to 4, an alkoxy group having carbon atoms of from 1 to 4 and an alkoxycarbonyl group having carbon atoms of from 2 to 5.

(1) Compounds (I) wherein n is 1 to 5 can be easily produced by, for example, reacting monometal salts of ascochlorin, say sodium or potassium salt thereof, with a halogeno aliphatic acid ester, and optionally hydrolyzing the reaction product. Ordinary organic solvents may be used as a reaction solvent, for example, alcohols such as methanol and ethanol, ketones such as acetone, ethers such as diethyl ether and tetrahydrofuran, aromatic hydrocarbons such as benzene and toluene, halogenated hydrocarbons such as chloroform, acid amides such as dimethylformamide, and dimethyl sulfoxide. Alcohols, dimethylformamide and acetone are ordinarily used because of their inertness, ease of handling (safeness) and low price. The reaction temperature can be selected from a wide range that includes room temperature up to the boiling points of solvents. The resulting alkoxycarbonyl alkyl ether of ascochlorin can be hydrolyzed into derivatives of free carboxylic acid type under mild alkaline conditions, say, in the presence of a base such as potassium carbonate or sodium carbonate. Hydrolysis under acidic conditions should be avoided since it easily gives undesirable by-products.

(2) Compound (I) wherein n is 0 can be produced by, for example, reacting ascochlorin with a reactive acid derivative such as an acid halide, an acid anhydride or sometimes a cyanate or an isocyanate in the presence or absence of a condensing agent (e.g. tertiary amines such as pyridines, triethylamine and dimethyl aniline, and alkali bases). The reaction may proceed without solvents, but usually it is effected in solvents in order to achieve high yield and assure ease of handling. Solvents that do not react with the reactive acid derivative are used. Suitable solvents include benzene, dimethylformamide, ethers, chloroform and acetone. The condensing agent may also be used as a solvent. The reaction temperatures may be selected from a wide range that includes room temperature up to the boiling points of solvents. Using an excess of reactive acid derivative should be avoided since it may give rise to 2,4-bis-o-acyl derivative of ascochlorin. But little of the bis form of ascochlorin is produced under the reaction conditions shown in the Examples. The end product can be purified by any of the conventional methods such as recrystallization, column chromatography and extraction from solvents.

The compounds of the present invention thus produced have the following desired pharmacological activities and hence are useful as medicine.

1. When they are added to an incubation medium of adipose tissue, the compounds promote significantly the uptake of glucose in an insulin-dependent manner to a concentration of $10^{-5}M$ that is a physiologically attainable level. This activity is specific for tissues that glucose uptake is insulin-dependent, and it is not observed in tissues such as liver and kidney where glucose uptake is independent on insulin but dependent on glucose concentration. However, the compounds also enhance the glucose metabolism such as conversion of glucose to carbon dioxide in liver and kidney slices. These facts suggest that the compounds of the present invention enhance the insulin sensitivity in insulin-dependent peripheral tissues.

The effect of the compounds of the present invention on carbohydrate and lipid metabolism are also observed in vivo when they are administered orally to laboratory animals. When they are administered to normal rats and mice orally for a given period, the levels of glucose and lipids in blood are decreased significantly. This fact indicates the effectiveness of the compounds in alleviating hypercaloremia that accompanies diabetes mellitus and atherosclerosis. In fact, the compounds proved very effective on diabetic animal models. For example, hereditary obese diabetic mice, strain C 57BL/KsJ (db+/db+), shows similar symptoms to human adult-onset diabetes mellitus (type II diabetes mellitus) such as hyperglycemia, obesity, peripheral insulin resistance, polydipsia and polyurea, and excretion of urine glucose. Conventional antidiabetic drugs such as sulfony ureas and biguanides are completely ineffective on this animal model. But the compounds of the present invention were capable of supressing polydipsia and polyurea, and remarkably reducing the blood glucose and lipid levels without affecting diet intake. It is of particular note that the compounds reduced the daily excretion of urine glucose by 90% Similar effects were observed in animals with diabetes mellitus induced by an injection of alloxane and streptozotocin. It is therefore clear that the compounds of the present invention are effective on diabetes mellitus and are capable of improving carbohydrate and lipid metabolism.

The mechanism of action of the compounds of the present invention was evaluated using adipocytes derived from diabetic animals which orally received the compounds for a given period. When 4-O-carboxymethyl ascochlorin was orally given once daily for 2 weeks to streptozotocin-diabetic rats, the treatment increased $^{125}$I-insulin binding to adipocytes above normal and diabetic control levels. Moreover, 2-deoxyglucose uptake, and conversion of glucose to carbon dioxide and lipids in the adipocytes were greatly increased by the treatment.

The hereditary obese diabetic mouse, strain C 57BL/KsJ (db+/db+), is an excellent model of human type II diabetes mellitus. When the diabetic mice were treated with 4-O-carboxymethyl-ascochlorin orally for 1 week, the treatment caused 1.5–3.0 fold increment in $^{125}$I-insulin binding to the adipocytes above age-matched untreated diabetic controls. Also the treatment increased 2-deoxyglucose uptake, and conversion of glucose to carbon dioxide and lipid.

Therefore, it is evident that the treatment with the compounds of the present invention increases insulin binding to the receptor and improves the impaired glucose metabolism of both insulin-deficient (type I) and insulin-resistant (type II) diabetic animal models.

Potentiation of insulin action by the compounds of the present invention is corroborated by restoration of hepatic lipogenesis in streptozotocin-diabetic mice. Streptozotocin diabetic mice greatly deteriolate hepatic lipogenesis due to insulin deficiency. When 4-O-carboxymethylascochlorin or 4-O-nicotinoylascochlorin were orally given to the diabetic mice for a week, the incorporation of acetate into hepatic total fatty acid and triglyceride restored to normal control levels in vivo, while the incorporation of the untreated diabetic controls dropped to one half of the normal.

Therefore, the mechanism of action of the compounds of the present invention resides in potentiating insulin action in insulin-dependent peripheral tissues on one hand, and in replacing partially the insulin action on the other.

2. The other remarkable effect of the compounds of the present invention is their activity against malignant tumors. Transplantable leukemia L-1210 that originated from spontaneous leukemia in DBA/2 mice is a malignant tumor frequently used in screening anti-tumor agents. This tumor is so malignant that all mice intraperitoneally transplanted with 100 cells of the tumor die of the tumor within two weeks. However, a single administration of some of the compounds of the present invention one week before the transplantation of the tumor proved perfectly effective against L-1210 in mice. This effect is not observed in the conventional anti-tumor agents and immunomodulators or immunostimulants.

The compounds of the present invention are also capable of prolonging significantly the life span of mice bearing experimental tumors such as Ehrlich, S-180, MethA, L-121 and P-388 under the conditions conventionally used to evaluate the efficacy of anti-tumor agents.

The compounds of the present invention may be used alone, but preferably they are formulated in preparations suitable for parenteral or oral administration by dissolving them in water after neutralization with alkalis or mixing them with suspending agents, excipients or other adjuvants. Preferred forms of preparations include injections, powders, granules, tablets, sugar-coated tablets, pills, capsules and suppositories. These preparations are made by any conventional method, such as using excipients or adjuvants selected from among lactose, sucrose, starches, glucose, cellulose, methyl cellulose, carboxymethyl cellulose, magnesium stearate, lauryl sulfate, talc, vegetable oils, octyldecyl triglyceride, sodium bicarbonate, polysolvates, polyethylene glycol, lecithin and mixtures thereof.

Preparations for oral administration preferably contain 10 to 55% by weight of the active ingredient, and injections preferably contain 1 to 20% by weight of the active ingredient. The toxicity of the compounds of the present invention is very weak, and their acute toxicity ($LD_{50}$) against rats and mice is not less than 0.5 to 10 g/kg for oral administration and not less than 150 to 500 mg/kg for parenteral administration. The dose of the compounds of the present invention as a pharmaceutical agent varies with the specific disease and its severity, but the desired object can be attained by 5 to 1000 mg of an injection per adult per day, 30 to 3000 mg of an orally administered medicine and 5 to 1000 mg of a suppository.

Two examples of the method of preparing a pharmaceutical agent from the compounds of the present invention are given below:

1. A sterilized powder (92.5 mg) of the compounds of the present invention is added to 10 ml of sterile distilled water having 158 mg of diethyl aminoethanol dissolved therein, and the mixture is heated at 80° C. for 5 minutes to make a solution. The solution is either directly injected into the vein or instilled intravenously as a mixture with an infusion solution or glucose solution.

2. A hundred parts of fine particles (ca. $2\mu$ in size) of the compounds of the present invention is mixed intimately with 88 parts of lactose, 100 parts of corn starch, 2 parts of HPC-SL, 50 parts of L-HPC (PO-30), 33 parts of crystalline cellulozse, 5 parts of calcium stearate and 10 parts of talc, and the mixture is stamped into tablets (8 mm in diameter and 250 mg in weight) with a tableting machine.

EXAMPLE 1

Ascochlorin (81 g, 0.2 mol) was dissolved in 600 ml of dimethylformamide. To the solution, 7.5 g of 60% sodium hydride (oily) was added in small portions. To the resulting sodium salt solution, 33.4 g (0.2 mol) of ethyl bromoacetate was added. The mixture was left at room temperature overnight, and 0.8 g of 60% sodium hydride and 3.34 g of ethyl bromoacetate were added. The mixture was left overnight and concentrated under vacuum. The oily residue was mixed thoroughly with 1000 ml of 1% hydrochloric acid and 1000 ml of chloroform. The mixture was transferred to a separating funnel, shaken vigorously and left to stand. The chloroform underlayer was separated, dried with anhydrous sodium sulfate and concentrated to dryness. To the oily residue, 1000 ml of methanol was added and the mixture was left overnight. The resulting crystal was separated and dried. A yellowish crystal of the end compound having a melting point of 114° C. was obtained in an amount of 61.3 g. The mother liquor was concentrated and left to stand to provide more of the end compound (13.7 g). A crystal (m.p. 114° C.) formed by recrystallization from methanol had the following analysis for $C_{27}H_{38}ClO_6$:

Calculated (%): C, 66.05; H, 7.18. Found (%): C, 66.21; H, 7.06.

Proton NMR spectrum (100 MHz, CDCl$_3$, TMS as internal standard) δ: 0.69 (3H, s), 0.80 (3H, d), 0.83 (3H, d), 1.32 (3H, t), 1.90 (3H, s), 1.6–2.0 (3H, m), 2.3–2.5 (3H, m), 2.63 (3H, s), 3.61 (2H, d), 4.30 (2H, q), 4.59 (2H, s), 5.37 (1H, d), 5.45 (1H, t), 5.90 (1H, d), 10.26 (1H, s), 12.54 (1H, s).

Formula of the end compound:

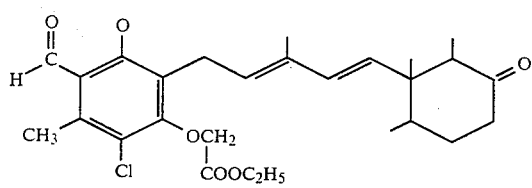

EXAMPLE 2

Ascochlorin (20.25 g) was dissolved in 350 ml of dimethylformamide. To the solution, 2.0 g of 60% sodium hydride (oily) was added in small portions. To the resulting sodium salt solution, 7.65 g of methyl bromoacetate was added. The mixture was left at room temperature overnight, and 0.2 g of 60% sodium hydride and 0.77 g of methyl bromoacetate were added. The mixture was left a few days and concentrated under vacuum. The oily residue was mixed thoroughly with 400 ml of 1% hydrochloric acid and 400 mg of chloroform. The mixture was transferred to a separating funnel, shaken vigorously and left to stand. The chloroform layer was separated, dried with anhydrous sodium sulfate and concentrated to dryness. To the oily residue, 150 ml of methanol was added and the mixture was heated to form a solution, which was then left overnight. The resulting crystal was filtered off and dried with air. A pale yellow crystal of the end compound having a melting point of 128° C. was obtained in an amount of 15.76 g (yield: 66%). Any residual end compound in the mother liquor could be isolated by column chromatography on silica gel. A crystal (m.p. 128° C.) formed by recrystallization from methanol had the following analysis for $C_{26}H_{33}ClO_6$:

Calculated (%): C, 65.47; H, 6.97. Found (%): C, 65.60; H, 6.96.

Proton NMR spectrum (100 MHz, CDCl$_3$, TMS as internal standard) δ: 0.69 (3H, s), 0.80 (3H, d), 0.83 (3H, d), 1.89 (3H, s), 1.6–2.0 (3H, m), 2.3–2.5 (3H, m), 2.63 (3H, s), 3.60 (2H, d), 3.83 (3H, t), 4.60 (2H, d), 5.36 (1H, d), 5.45 (1H, t), 5.89 (1H, d), 10.26 (1H, s), 12.54 (1H, s)

Formula of the end compound:

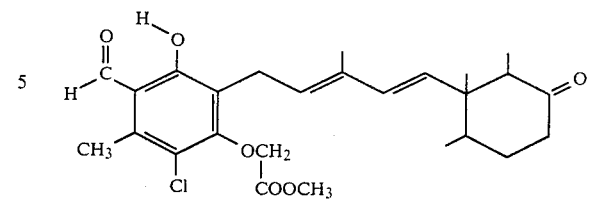

EXAMPLE 3

Metal sodium (0.23 g) was dissolved in 50 ml of ethanol. To the resulting solution, 4.05 g of ascochlorin, 1.84 g of ethyl bromoacetate and 40 ml of ethanol were added. The mixture was refluxed on a hot water bath for 10 hours, and concentrated under vacuum to dryness. The residue was thoroughly mixed with 50 ml of 1% hydrochloric acid and 50 ml of chloroform. The mixture was transferred to a separating funnel, shaken vigorously and left to stand. The chloroform layer was separated, dried with anhydrous sodium sulfate and concentrated under vacuum to dryness. The oily residue was recrystallized from methanol to give 2.5 g of a crystal of the same end compound as produced in Example 1.

EXAMPLE 4

Twenty grams of the 4-O-ethoxycarbonylmethylated ascochlorin produced in Example 1 was dissolved in 600 ml of methanol under heating. The solution was cooled to 35° C. and mixed under stirring with 80 ml of water having 20 g of anhydrous calcium carbonate dissolved therein. Two hours later, the mixture was subjected to suction filtration and 100 ml of water was added to the filtrate. The mixture was neutralized with 10% hydrochloric acid. The neutralized mixture was concentrated under vacuum to a volume of about 200 ml. The concentrated mixture was dissolved in 100 ml of water and adjusted to a pH of 2.0 with 10% hydrochloric acid. To the solution, 200 ml of chloroform was added and the mixture was shaken vigorously and left to stand. The chloroform underlayer was separated, dried with anhydrous sodium sulfate and concentrated under vacuum. The oily residue was dissolved in about 50 ml of methanol, and water was added until the solution became turbid. A seed crystal of the end compound was added to the solution and the mixture was left to stand overnight. The resulting crystal was filtered off and dried to give 13.8 g of the end compound having a melting point of 147° C. A crystal (m.p. 147° C.) produced by recrystallization from hydrous methanol had the following analysis for $C_{25}H_{31}ClO_6$:

Calculated (%): C, 64.86; H, 6.75. Found (%): C, 64.65; H, 6.71.

Proton NMR spectrum (100 MHz, CDCl$_3$, TMS as internal standard) δ: 0.70 (3H, s), 0.80 (3H, d), 0.83 (3H, d), 1.91 (3H, s), 1.6–2.0 (3H, m), 2.3–2.5 (3H, m), 2.64 (3H, s), 3.61 (2H, d), 4.66 (2H, s), 5.39 (1H, d), 5.46 (1H, t), 5.91 (1H, d), 10.26 (1H, s), 10.55 (1H, s), 12.53 (1H, s)

Formula of the end compound:

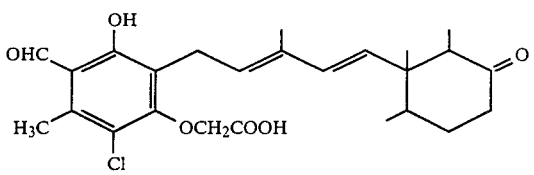

EXAMPLE 5

Ascochlorin (20.25 g) was reacted with 10.41 g of ethyl 2-bromopropionate as in Example 1. The reaction product was treated as in Example 1 and the resulting oily mixture was isolated by column chromatography on silica gel. The end compound could be eluted from the column with dichloromethane containing 3% ethyl acetate. A viscous oil of the end compound was obtained in an amount of 8.2 g.

Proton NMR spectrum (100 MHz, CDCl$_3$, TMS as internal standard) δ: 0.69 (3H, s), 0.80 (3H, d), 0.83 (3H, d), 1.27 (3H, t), 1.60 (3H, d), 1.90 (3H, s), 1.6-2.0 (3H, m), 2.3-2.5 (3H, m), 2.62 (3H, s), 3.62 (2H, d), 4.21 (2H, q), 4.98 (1H, q), 5.37 (1H, d), 5.45 (1H, t), 5.90 (1H, d), 10.26 (1H, s), 12.54 (1H, s).

Formula of the end compound:

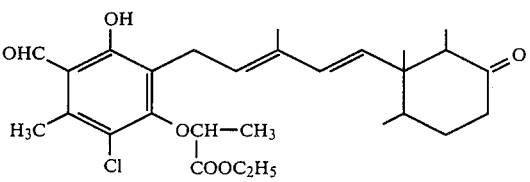

EXAMPLE 6

Ascochlorin (12.15 g) was dissolved in 150 ml of dimethylformamide. To the solution, 1.2 g of 60% sodium hydride (oily) was added in small portions. To the resulting sodium salt solution, 6.27 g of n-butyl 2-bromopropionate was added. The mixture was left at room temperature for a few days, and 0.3 g of 60% sodium hydride and 2.2 g of n-butyl bromopropionate were added, and the resulting mixture was left for a few days. The reaction liquor was concentrated to dryness under vacuum. The residue was mixed thoroughly with 250 ml of 1% hydrochloric acid and 250 ml of chloroform. The mixture was transferred to a separating funnel, shaken vigorously and left to stand. The chloroform layer was separated, dried with anhydrous sodium sulfate and concentrated to dryness. The oily residue was isolated by column chromatography on silica gel to give a pure form of the end compound. The compound was left to stand at room temperature for an extended period while it was crystallized gradually. The crystal had a melting point between 50° and 65° C. and its yield was 9.53 g. A product recrystallized from methanol had the following analysis for C$_{30}$H$_{41}$ClO$_6$:

Calculated (%): C, 67.59; H, 7.75. Found (%): C, 67.68; H, 7.73.

Proton NMR spectrum (100 MHz, CDCl$_3$, TMS as internal standard) δ: 0.69 (3H, s), 0.81 (3H, d), 0.83 (3H, d), 0.91 (3H, t), 1.2-2.0 (7H, m), 1.61 (3H, d), 1.91 (3H, s), 2.3-2.5 (3H, m), 2.62 (3H, s), 3.4-3.8 (2H, m), 4.16 (2H, t), 4.99 (1H, q), 5.37 (1H, d), 5.49 (1H, t), 5.91 (1H, d), 10.24 (1H, s), 12.56 (1H, s).

Formula of the end compound:

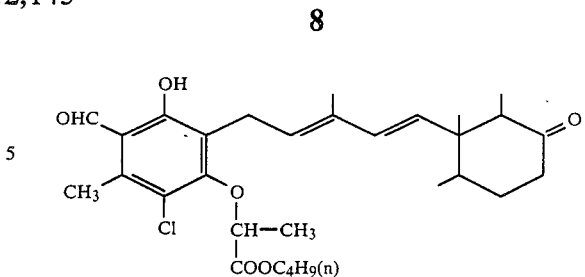

EXAMPLE 7

Ascochlorin (12.15 g) was dissolved in 150 ml of dimethylformamide. To the solution, 1.1 g of 60% sodium hydride (oily) was added in small portions. To the resulting sodium salt solution, 5.85 g of ethyl 2-bromobutyrate was added, and the mixture was heated at 90° C. for 4 hours. To the mixture, 340 mg of 60% sodium hydride and 1.64 g of ethyl 2-bromoacetate were added and the mixture was heated at 90° C. for 4 hours. The reaction liquor was concentrated under vacuum to dryness, and the residue was mixed thoroughly with 300 ml of 1% hydrochloric acid and 300 ml of chloroform. The mixture was transferred to a separating funnel, shaken vigorously and left to stand. The chloroform layer was separated, dried with anhydrous sodium sulfate and concentrated to dryness. The oily residue was isolated by column chromatography on silica gel. The column was eluted with dichloromethane containing 3% ethyl acetate, and fractions of the end compound were collected and concentrated to dryness. A viscous oil of the end compound was obtained in an amount of 6.8 g.

Proton NMR spectrum (100 MHz, CDCl$_3$, TMS as internal standard) δ: 0.70 (3H, s), 0.81 (3H, d), 0.83 (3H, d), 1.05 (3H, t), 1.25 (3H, t), 1.92 (3H, s), 1.4-2.2 (5H, m), 2.3-2.5 (3H, m), 2.61 (3H, s), 3.4-3.9 (2H, m), 4.19 (2H, t), 4.93 (1H, t), 5.36 (1H, d), 5.48 (1H, t), 5.91 (1H, d), 10.23 (1H, s), 12.55 (1H, s).

Formula of the end compound:

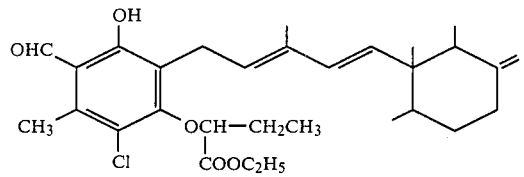

EXAMPLE 8

Ascochlorin (12.15 g) was dissolved in 200 ml of dimethylformamide. To the solution, 1.2 g of 60% sodium hydride (oily) was added in small portions. To the resulting sodium salt solution, 5.9 g of ethyl 4-bromobutyrate was added, and the mixture was heated at between 90° and 100° C. for 3 hours. To the mixture, 0.3 g of 60% sodium hydride and 2 g of ethyl 4-bromobutyrate were added, and the resulting mixture was heated for another ten hours. The reaction liquor was concentrated under vacuum to dryness, and the residue was mixed thoroughly with 200 ml of 1% hydrochloric acid and 200 ml of chloroform. The mixture was transferred to a separating funnel, shaken vigorously and left to stand. The chloroform layer was separated, dried with anhydrous sodium sulfate and concentrated umder vacuum to dryness. The oily residue was isolated by column chromatography on silica gel. A viscous oil of the end compound was obtained in 8.6 g.

Proton NMR spectrum (100 MHz, CDCl₃, TMS as internal standard) δ: 0.69 (3H, s), 0.80 (3H, d), 0.83 (3H, d), 1.26 (3H, t), 1.92 (3H, s), 1.6-2.8 (7H, m), 2.62 (3H, s), 3.50 (2H, d), 3.98 (2H, t), 4.16 (2H, q), 5.37 (1H, d), 5.45 (1H, t), 5.90 (1H, d), 10.22 (1H, s), 12.52 (1H, s).

Formula of the end compound:

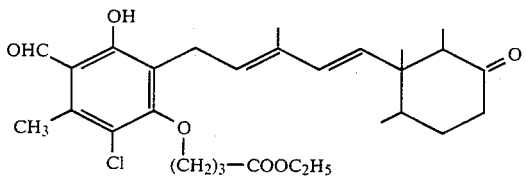

EXAMPLE 9

Four grams of the 4-O-(1-ethoxycarbonylethyl) ester of ascochlorin obtained in Example 5 was hydrolyzed and post-treated as in Example 4. The oily residue containing the end compound was purified by column chromatography on silica gel (methanol:chloroform = 1:20). The resulting end product (3.4 g) was a non-crystalline solid whose melting point was not clearly defined.

Proton NMR spectrum (100 MHz, CDCl₃, TMS as internal standard) δ: 0.70 (3H, s), 0.80 (3H, d), 0.83 (3H, d), 1.60 (3H, d), 1.90 (3H, s), 1.6-2.0 (3H, m), 2.3-2.5 (3H, m), 2.62 (3H, s), 3.62 (2H, d), 4.98 (1H, q), 5.37 (1H, d), 5.45 (1H, t), 5.90 (1H, d), 10.20 (1H, s), 10.25 (1H, s), 12.50 (1H, s).

Formula of the end compound:

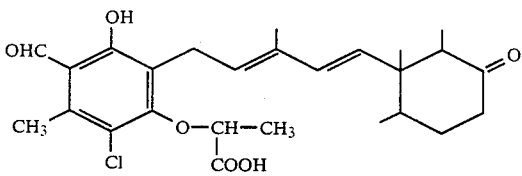

EXAMPLE 10

Five grams of the 4-O-(3-ethoxycarbonyl)propyl ester of ascochlorin obtained in Example 8 was hydrolyzed and post-treated as in Example 4. The oily residue containing the end compound was purified by column chromatography on silica gel (ethyl acetate:chloroform = 1:10).

Proton NMR spectrum (100 MHz, CDCl₃, TMS as internal standard) δ: 0.69 (3H, s), 0.80 (3H, d), 0.83 (3H, d), 1.92 (3H, s), 1.6-2.8 (7H, m), 2.62 (3H, s), 3.50 (2H, d), 3.98 (2H, t), 5.37 (1H, d), 5.45 (1H, t), 5.90 (1H, d), 10.22 (1H, s), 10.50 (1H, s), 12.52 (1H, s).

Formula of the end compound:

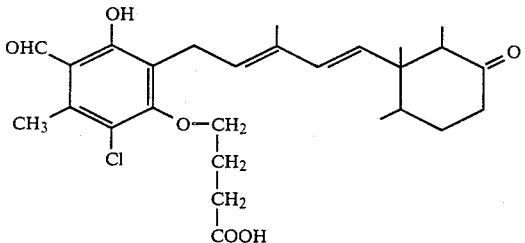

EXAMPLE 11

Ascochlorin (10 g, 24.7 milli-mol) was dissolved in 50 ml of dry pyridine. Under cooling with ice water, 6.6 g (37.07 milli-mol) of nicotinic acid chloride hydrochloride was added in small portions with stirring. Then, the temperature in the reaction vessel was increased gradually to room temperature under continued stirring. After stirring for a whole day, the reaction liquor was concentrated under vacuum to dryness. The residue was mixed thoroughly with chloroform-water, and the mixture was transferred to a separating funnel, shaken vigorously and left to stand. The chloroform layer was separated, washed with water thoroughly and dried with anhydrous sodium sulfate. The dried product was filtered and the filtrate was again concentrated under vacuum. The oily residue was isolated by column chromatography on silica gel. The column was eluted with chloroform containing 1-2% methanol or benzene containing 5% ethyl acetate, and fractions containing the end compound were collected and concentrated under vacuum to obtain a viscous oily product. The product was dissolved in ethanol and the solution was left to stand. A crystal of the end compound was produced in 9.6 g (76.3%). A sample of the compound recrystallized from ethanol had a melting point of 159°-160° C. and had the following analysis for C₂₉H₃₂O₅ClN:

Calculated (%): C, 68.29; H, 6,32; N, 2.75. Found (%): C, 68.23; H, 6.36; N, 2.80.

Formula of the end compound:

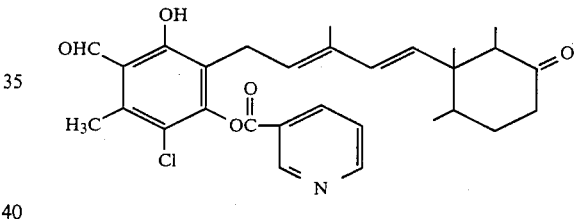

EXAMPLE 12

A mixture of ascochlorin (40.5 g, 0.1 mol), dry benzene (500 ml) and dry pyridine (24 ml, 0.297 mol) was put in a 1000-ml capacity conical flask and shaken to form a uniform solution. To the solution, 25.22 g (0.142 mol) of nicotinic acid chloride hydrochloride was added at room temperature under stirring with a magnetic stirrer. After stirring for 3 hours, the suspended particles of the resulting pyridine hydrochloride was filtered off. The filtrate was subjected to three cycles of adding 500 ml of water, shaking the solution and removing the aqueous layer. If the removal of the aqueous layer is difficult because the shaken solution becomes turbid, add a solution of sodium chloride. The benzene layer was separated, dried with anhydrous sodium sulfate and the solvent was distilled off under vacuum to give a viscous oily product. The oil was dissolved in 800 ml of ethanol and the solution was left to stand to give a crystal of the end compound (41.0 g, 80.4%). A sample recrystallized from ethanol had a melting point between 159° and 160° C. and the following analysis for C₂₉H₃₂O₅ClN:

Calculated (%): C, 68.29; H, 6.32; N, 2.75. Found (%): C, 68.21; H, 6.32, N, 2.76.

Proton NMR spectrum (100 MHz, CDCl₃, TMS as internal standard) δ: 0.69 (3H, s), 0.80 (3H, d), 0.82 (9H, d), 1.70 (3H, s), 3.55 (2H, d), 5.37 (1H, d), 5.54 (1H, t), 5.84 (1H, d), 7.49 (1H, m), 8.55 (1H, d), 8.96 (1H, d), 9.42 (1H, s), 10.34 (1H, s), 12.60 (1H, s).

Formula of the end compound:

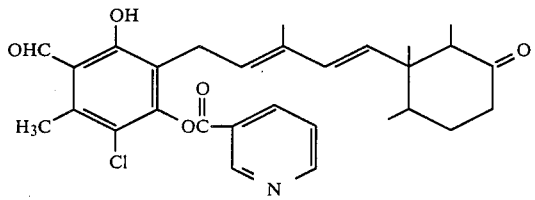

EXAMPLE 13

Ascochlorin (20 g, 49.4 milli-mol) was dissolved in dry pyridine (100 ml). To the solution, 6.9 g of diethylcarbamoyl chloride (49.9 milli-mol) was added and the mixture was refluxed for about 5 hours. Then, another 6.9 g of diethylcarbamoyl chloride was added and the mixture was further refluxed. When it was confirmed that ascochlorin was no longer present in the reaction system, the reaction liquor was concentrated under vacuum to dryness. The residue was mixed thoroughly with water-benzene, and the mixture was transferred to a separating funnel, shaken vigorously, and left to stand. The benzene layer was separated, washed with water thoroughly, dried with anhydrous sodium sulfate, and the solvent was distilled off. The oily residue was isolated by column chromatography on silica gel. The column was eluted with benzene containing 5% ethyl acetate, and fractions of the end compound were collected and concentrated to dryness to give a viscous oily product. The product was dissolved in ethanol and the solution was left to stand in a cool place until a crystal of the end compound was formed in an amount of 16 g (64%). The crude crystal was recrystallized from ethanol to produce a pure crystal having a melting point between 125° and 127° C. and the following analysis for $C_{28}H_{38}O_5ClN$:

Calculated (%): C, 66.72; H, 7.60; N, 2.78. Found (%): C, 66.85; H, 7.67; N, 2.80.

Proton NMR spectrum (100 MHz, CDCl$_3$, TMS as internal standard) δ: 0.67 (3H, s), 0.79 (3H, d), 0.82 (3H, d), 1.12-1.36 (6H, m), 1.86 (3H, s), 2.20-2.50 (3H, m), 2.63 (3H, s), 3.30-3.60 (6H, m), 5.35 (1H, d), 5.42 (1H, t), 5.89 (1H, d), 10.28 (1H, s), 12.53 (1H, s).

Formula of the end compound:

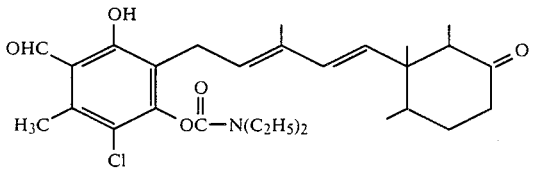

EXAMPLE 14

Ascochlorin (10 g, 24.7 milli-mol) was dissolved in dry pyridine (100 ml). To the solution, 8.0 g (39.0 milli-mol) of para-chlorophenoxyacetyl chloride was added, and the mixture was heated at between 60° and 70° C. for 5 hours under stirring. Then, another 1.0 g (4.9 milli-mol) of para-chlorophenoxyacetyl chloride was added, and the mixture was heated at between 60° and 70° C. for 5 hours under stirring. The reaction liquor was concentrated under vacuum to dryness and subsequently treated as in Example 3. The oily residue containing the end compound was isolated by column chromatography on silica gel, and the so purified product was dissolved in ethanol and the solution was left at room temperature until a crystal of the end compound was formed in an amount of 4.7 g (33.2%). A sample recrystallize from methanol had a melting point between 122° and 124° C. and the following analysis for $C_{31}H_{34}O_6Cl_2$:

Calculated (%): C, 64.92; H, 5.98. Found (%): C, 64.86; H, 5.95.

Proton NMR spectrum (100 MHz, CDCl$_3$, TMS as internal standard) δ: 0.70 (3H, s), 0.80 (3H, d), 0.83 (3H, d), 1.87 (3H, s), 2.66 (3H, s), 3.40 (2H, d), 4.93 (2H, s), 5.20 (1H, t), 5.38 (1H, d), 5.84 (1H, d), 6.92 (2H, d), 7.30 (2H, d), 10.30 (1H, s), 12.56 (1H, s).

Formula of the end compound:

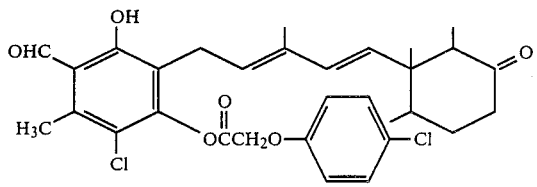

EXAMPLE 15

Ascochlorin (7 g, 17.3 milli-mol) was dissolved in dry pyridine (70 ml). To the solution, 8.0 g (46.9 milli-mol) of para-methoxybenzoyl chloride was added, and the mixture was refluxed for 5 hours. The mixture was subsequently treated as in Example 3, and the resulting end compound was dissolved in ethanol, and the solution was left to stand at room temperature until a crystal of the end compound was obtained in an amount of 3.8 g (40.8%). The crude crystal was recrystallized from ethanol to give a product having a melting point between 155° and 156° C. and the following analysis for $C_{31}H_{35}O_6Cl$:

Calculated (%): C, 69.07; H, 6.54. Found (%): C, 68.82; H, 6.56.

Proton NMR spectrum (100 MHz, CDCl$_3$, TMS as internal standard) δ: 0.68 (3H, s), 0.79 (3H, d), 0.82 (3H, d), 1.70 (3H, s), 2.67 (3H, s), 3.55 (2H, d), 3.91 (3H, s), 5.35 (1H, d), 5.50 (1H, t), 5.86 (1H, d), 7.01 (2H, d), 8.16 (2H, d), 10.32 (1H, s), 12.57 (1H, s).

Formula of the end compound:

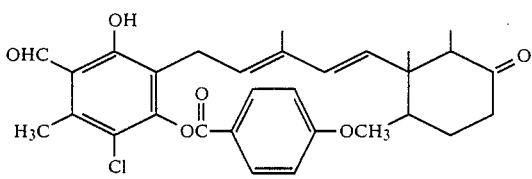

EXAMPLE 16

Ascochlorine (10 g, 24.7 milli-mol) was dissolved in dry pyridine (100 ml). To the solution, 5.9 g (29.6 milli-mol) of para-methoxycarbonyl benzoyl chloride was added and the mixture was heated at between 60° and 70° C. under stirring for 7 hours. To the mixture, another 5.9 g (29.6 milli-mol) of para-methoxycarbonyl benzoyl chloride was added, and the mixture was heated at between 60° and 70° C. for another 7 hours. The mixture was subsequently treated as in Example 3, and the resulting oily end compound was dissolved in ethanol, and the solution was left to stand at room temperature until a crystal of the end compound was obtained in an amount of 3.3 g (23.6%). The crude crystal was recrystallized from ethanol to give a product having a melting point between 147° and 148° C. and the following analysis for $C_{32}H_{35}O_7Cl$:

Calculated (%): C, 67.78; H, 6.22. Found (%): C, 67.78: H, 6.30.

Proton NMR spectrum (100 MHz, CDCl$_3$, TMS as internal standard) δ: 0.68 (3H, s), 0.78 (3H, d), 0.81 (3H, d), 1.59 (3H, s), 2.69 (3H, s), 3.55 (2H, d), 3.99 (3H, s), 5.35 (1H, d), 5.53 (1H, t), 5.84 (1H, d), 10.34 (1H, s), 12.60 (1H, s), 8.14 (4H, m).

Formula of the end compound:

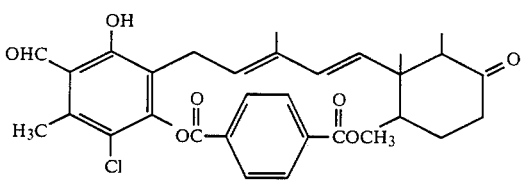

EXAMPLE 17

Ascochlorin (20 g, 49.4 milli-mol) was dissolved in dry pyridine (100 ml). To the solution, 13.2 g (73.7 milli-mol) of isonicotinic acid chloride hydrochloride was added, and the mixture was heated at 70° C. for 4 hours under stirring. Then, another 5 g (28.1 milli-mol) of isonicotinic acid chloride hydrochloride was added, and the mixture was further heated at 70° C. for 7 hours under stirring. The mixture was subsequently treated as in Example 3, and the resulting oily residue containing the end compound was dissolved in ethanol, and the solution was left in a cool place until a crystal of the end compound was obtained in an amount of 7.2 g (28.6%). The crude crystal was recrystallized from ethanol to give a product having a melting point between 111° and 113° C. and the following analysis for $C_{29}H_{32}O_5ClN$:

Calculated (%): C, 68.30; H, 6.28. Found (%): C, 68.27; H, 6.31.

Proton NMR spectrum (100 MHz, CDCl$_3$, TMS as internal standard) δ: 0.68 (3H, s), 0.78 (3H, d), 0.81 (3H, d), 1.67 (3H, s), 2.69 (3H, s), 3.45 (2H, d), 5.28 (1H, d), 5.35 (1H, t), 5.83 (1H, d), 8.00 (2H, d), 8.80 (2H, d), 10.34 (1H, s), 12.61 (1H, s).

Formula of the end compound:

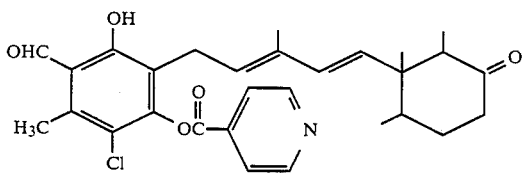

EXAMPLE 18

Ascochlorin (5 g, 12.35 milli-mol) was dissolved in dry pyridine (50 ml). To the solution, 4.4 g (24.7 milli-mol) of picolinic acid chloride hydrochloride was added and the mixture was heated at 60° C. for 3 hours under stirring. Then, another 1.5 g (8.43 milli-mol) of picolinic acid chloride hydrochloride was added and the mixture was heated at 60° C. for another 7 hours under stirring. The heated mixture was subsequently treated as in Example 3. The resulting oily end product was dissolved in ethanol and the solution was left at room temperature until a crystal of the end compound was obtained in an amount of 2.0 g (32%). The crude crystal was recrystallized from ethanol to give a product having a melting point between 150° and 152° C. and the following analysis for $C_{29}H_{32}O_5ClN$:

Calculated (%): C, 68.30; H, 6.28. Found (%): C, 68.30; H, 6.25.

Proton NMR spectrum (100 MHz, CDCl$_3$, TMS as internal standard) δ: 0.66 (3H, s), 0.77 (3H, d), 0.79 (3H, d), 1.76 (3H, s), 2.68 (3H, s), 3.55 (2H, d), 5.26 (1H, d), 5.41 (1H, t), 5.83 (1H, d), 7.62 (1H, m), 7.96 (1H, m), 8.26 (1H, d), 8.87 (1H, d), 10.33 (1H, s), 12.59 (1H, s).

Formula of the end compound:

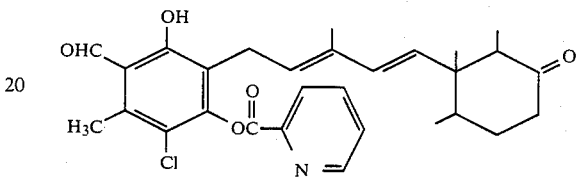

EXAMPLE 19

Five-week-old ddY male mice (n=10) were given for one week a diet (CE-2 from Nippon Crea Co., Ltd.) containing 0.1% of the sample compounds of the present invention indicated in Table 1. Blood was then withdrawn from the heart and the glucose and cholesterol levels in plasma were measured. The results are shown in Table 1.

TABLE 1

| Compound (Example No.) | plasma glucose (mg/dl) | total cholesterol in plasma (mg/dl) |
|---|---|---|
| 4 | 217.6 ± 12.2** | 107.9 ± 4.5** |
| 9 | 210.0 ± 10.7** | 106.7 ± 5.5** |
| 10 | 220.1 ± 6.8* | 115.7 ± 5.0* |
| 1 | 208.3 ± 13.1** | 105.7 ± 3.0** |
| 5 | 205.7 ± 8.2** | 109.7 ± 5.0** |
| 8 | 255.5 ± 17.0 | 115.0 ± 6.6** |
| control | 271.6 ± 0.4 | 135.9 ± 4.8 |

*P < 0.05,
**P < 0.01 (unpaired t-test)

EXAMPLE 20

Hereditary obese diabetic mice C 57BL/Ksj (db+/db+) were given for one week a diet containing 0.1% of 4-O-hydroxycarbonylmethyl ester of ascochlorin. The amounts of the diet taken drinking water, urine volume and urine glucose excreted were measured daily. The results are indicated in Table 2 in terms of mean value±standard error.

TABLE 2

| | one week prior to administration | one week administration |
|---|---|---|
| diet intake (g/mouse/day) | 6.35 ± 0.13 | 6.37 ± 0.28 |
| drinking water (ml/mouse/day) | 14.7 ± 0.3 | 10.4 ± 0.3*** (−29.3%) |
| urine volume (ml/mouse/day) | 5.95 ± 0.20 | 2.07 ± 0.23*** (−65.2%) |
| urine glucose (mg/mouse/day) | 579.5 ± 21.1 | 106.8 ± 19.5*** (−81.5%) |
| urine glucose | 97.4 ± 3.4 | 52.9 ± 5.52*** |

TABLE 2-continued

|  | one week prior to administration | one week administration |
|---|---|---|
| concentration (mg/ml) |  | (−45.7%) |

(n = 10)
***P < 0.001 (unpaired t-test)

EXAMPLE 21

Five-week-old ddY male mice were injected intraperitoneally with 130 mg/kg of streptozotocin. Twenty mice that proved strongly positive for urine glucose excretion by determination with Testape ® test paper from Eli Lily & Co. were allocated into two groups randomly. One group (n=10) was given for one week a diet (CE-2 from Nippon Crea Co., Ltd.) containing 0.1% of 4-O-ethoxycarbonylmethyl ester of ascochlorin, whereas the other group (n=10) was given only CE-2 for one week. Each group was allowed to take the diet and drink water freely. One week later, the levels of glucose, insulin, free fatty acid in serum and glycogen in liver were measured. The results are shown in Table 3.

TABLE 3

|  |  | Control | Treated |
|---|---|---|---|
| body weight | before feeding | 25.7 ± 0.4 | 25.5 ± 0.4 |
| (g/mouse) | after feeding | 28.0 ± 0.5 | 27.0 ± 0.6 ns |
| serum glucose (mg/dl) |  | 337.7 ± 23.0 | 250.6 ± 26.2* (−25.8%) |
| serum immunoreactive insulin (μU/ml) |  | 42.67 ± 4.61 | 26.60 ± 2.78** (−37..7%) |
| serum free fatty acid (mg/dl) |  | 44.29 ± 2.05 | 30.44 ± 1.22** (−31.3%) |

*P < 0.05,
**P < 0.01
Mean ± SE.

EXAMPLE 22

$10^6$ Cells of Ehrlich ascites tumor were transplanted in five-week-old ddY male mice and from the 24th hour onward, they were injected intraperitoneally the compounds indicated in Table 4 of the present invention once a day for 7 consecutive days. Each injection contained 2 mg of the test compounds. The efficacy of the compounds is indicated in Table 4 in terms of their life span.

TABLE 4

| Compound (Example No.) | Days survived | T/O (%) |
|---|---|---|
| 4 | >25.3 ± 4.65** | 163 |
| 9 | >28.8 ± 3.54** | 186 |
| 10 | 19.3 ± 10.12 | 125 |
| 1 | 19.3 ± 5.77 | 125 |
| 5 | >19.1 ± 1.97 | 123 |
| control | 15.5 ± 2.12 | 100 |

(n = 8)
**P < 0.01

EXAMPLE 23

Four-week-old BDF$_1$ female mice were injected intraperitoneally with suspensions of 2 mg of 4-O-hydroxycarbonylmethyl ester of ascochlorin in 1% tragacanth gum. A control group was injected only with 1% tragacanth gum. One week later, $10^2$ cells of L-1210 leukemia were transplanted in the mice. The results are shown in Table 5.

TABLE 5

|  | Died | Survived 50 days or more |
|---|---|---|
| Control | 20 | 0 |
| Treated | 13 | 7 |

P < 0.01 (as $x^2$)

EXAMPLE 24

Hereditary obese diabetic mice C 57BL/Ksj (db+/db+), 12 weeks old, were fed commercial pellet diet (CE-2 from Nippon Crea Co., Ltd.) for a week and they were treated with CE-2 pellet containing 0.05% of 4-O-nicotinoylascochlorin for a week. The daily amounts of the diet intake, drinking water, urine volume and urine glucose excreted were measured before and during the treatment. The results are shown in Table 6.

TABLE 6

|  | Control period | Treatment period |
|---|---|---|
| diet intake (g/mouse/day) | 4.85 ± 0.06 | 4.26 ± 0.39$^{NS}$ |
| drinking water (ml/mouse/day) | 14.55 ± 0.33 | 11.16 ± 0.52** (−23.30%) |
| urine volume (ml/mouse/day) | 8.60 ± 0.35 | 5.20 ± 0.36** (−39.5%) |
| urine glucose (mg/mouse/day) | 1129 ± 96 | 554 ± 43** (−50.9%) |
| urine glucose concentration (mg/ml) | 130.6 ± 5.7 | 106.3 ± 2.9** (−18.6%) |

(n = 5) Values are in mean ± SE
**P < 0.01

As the table shows, the treatment with 4-O-nicotinoyl ascochlorin improved polydipsis and polyurea and inhibited excretion of urine glucose.

EXAMPLE 25

Five-week-old ddY male mice were given for one week a diet (CE-2 from Nippon Crea Co., Ltd.) containing 0.05% of the compounds of the present invention indicated in Table 7. On the 7th day, the mice were sacrificed and the levels of lipid and glucose in their serum were measured. The results are shown in Table 7.

TABLE 7

|  | total cholesterol in serum (mg/dl) | neutral fat in serum (mg/dl) | free fatty acid in serum (mg/dl) | serum glucose (mg/dl) |
|---|---|---|---|---|
| 4-O—nicotinoyl ascochlorin | 106.7 ± 5.5* (−21.5%) | 102.0 ± 10.5* (−24.3%) | 21.2 ± 0.62* (−16.3%) | 228.0 ± 16.8* (−22.2%) |
| 4-O—diethylcarbamoyl ascochlorin | 121.2 ± 5.0+ (−10.8%) | 110.2 ± 16.4 (−18.2%) | 26.4 ± 0.58 (+4.3%) | 215.2 ± 5.7** (−26.6%) |
| 4-O—(p-chlorophenoxy) acetyl ascochlorin | 115.6 ± 9.8+ (−14.8%) | 99.4 ± 9.4* (−26.2%) | 24.9 ± 0.48 (−1.6%) | 209 ± 8.9** (−28.7%) |

TABLE 7-continued

| | total cholesterol in serum (mg/dl) | neutral fat in serum (mg/dl) | free fatty acid in serum (mg/dl) | serum glucose (mg/dl) |
|---|---|---|---|---|
| 4-O—(p-methoxybenzoyl) ascochlorin | 137.9 ± 4.1 (+1.4%) | 141.4 ± 21.3 (+4.9%) | 25.2 ± 1.89 (−0.4%) | 199.3 ± 8.6** (−31.9%) |
| 4-O—(p-methoxycarbonyl)-benzoyl ascochlorin | 129.6 ± 3.9 (−4.6%) | 136.3 ± 8.1 (+1.2%) | 21.8 ± 0.69+ (−15.9%) | 229.9 ± 17.0* (−21.5%) |
| 4-O—isonicotinoyl ascochlorin | 113.5 ± 7.8* (−16.5%) | 116.1 ± 13.8 (−13.8%) | 20.3 ± 0.77* (−19.8%) | 191.6 ± 13.2** (−34.6%) |
| 4-O—picolinyl ascochlorin | 138.4 ± 3.1 (+1.8%) | 117.6 ± 6.8 (−12.7%) | 23.5 ± 3.13 (−7.1%) | 247.7 ± 9.0* (−15.5%) |
| Control | 135.9 ± 4.8 | 134.7 ± 8.6 | 25.3 ± 1.62 | 293.0 ± 13.3 |

(n = 8)
Values are in mean ± SE
+P < 0.1
*P < 0.05
**P < 0.01

As the table shows, all compounds tested could reduce the serum glucose level. The three compounds, 4-O-nicotinoyl ascochlorin, 4-O-(p-chlorophenoxy)acetyl ascochlorin and 4-O-isonicotinoyl ascochlorin, could also reduce the lipid level in serum.

EXAMPLE 26

Five-week-old ddY male mice (n=7) were injected intraperitoneally 150 mg/kg of streptozotocin, and after 24 hours onward, they were given for one week a diet (CE-2 from Nippon Crea Co., Ltd.) containing 0.05% of 4-O-nicotinoyl ascochlorin. A control group was given only CE-2. On the 7th day, the animals were sacrificed and the levels of glucose and lipid in their plasma were measured. The results are shown in Table 8.

TABLE 8

| | Control | Treated |
|---|---|---|
| plasma glucose (mg/dl) | 453.6 ± 38.0 | 351.3 ± 23.0* (−23%) |
| neutral fat in plasma (mg/dl) | 189.8 ± 17.2 | 136.0 ± 12.3* (−28%) |
| free aliphatic acid in plasma (mg/dl) | 22.4 ± 1.4 | 20.5 ± 1.2 (−8%) |

Values are mean ± SE *P < 0.05

As the table shows, 4-O-nicotinoyl ascochlorin could inhibit significantly the increase in the levels of blood glucose and triglyceride in plasma in the streptozotocin diabetic models.

EXAMPLE 27

Hereditary obese diabetic mice C57BL/Ksj (db+/db+) were given for one week a diet (CE-2 from Nippon Crea Co., Ltd.) containing 0.05% of 4-O-nicotinoyl ascochlorin. A control group of the same age was given only CE-2. One week later, the animals were sacrificed and the levels of plasma glucose and lipid were measured. The results are shown in Table 9.

TABLE 9

| | Control | Treated |
|---|---|---|
| plasma free fatty acid (mg/dl) | 27.7 ± 1.8 | 26.1 ± 1.4 |
| plasma triglyceride (mg/dl) | 170.7 ± 16.3 | 115.5 ± 14.9* (−32.3%) |
| plasma glucose (mg/dl) | 453.6 ± 38.0 | 351.3 ± 23.0* (−23%) |
| immunoreactive insulin in plasma (μU/ml) | 236.6 ± 91.0 | 257.3 ± 91.3 |

(n = 7)
Values are mean ± SE
*P < 0.05

As the table shows, 4-O-nicotinoyl ascochlorin could reduce significantly the high plasma lipid and glucose levels in the diabetic mice.

What is claimed is:

1. An ascochlorin derivativee of the formula:

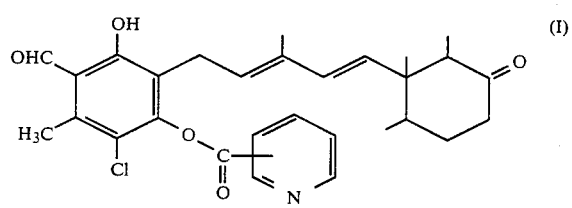

2. An ascochlorin derivative according to claim 1 which is 4-O-(3-pyridyl)carbonyl ascochlorin.

3. An ascochlorin derivative according to claim 1 which is 4-O-(4-pyridyl)carbonyl ascochlorin.

4. An ascochlorin derivative according to claim 1 which is 4-O-(2-pyridyl)carbonyl ascochlorin.

5. An anti-diabetic composition comprising an ascochlorin derivative of the formula

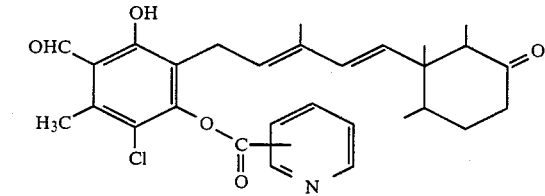

in an amount effective to treat diabetes, and a pharmaceutically acceptable carrier.

6. An anti-diabetic composition according to claim 5 in which said amount of the ascochlorin derivative is such that the derivative is administered in an amount between 5 and 3,000 mg per day.

7. A pharmaceutical composition according to claim 5 which is formulated in an injection, powder, granule, tablet, sugar-coated tablet, capsule, pill or suppository.

8. A pharmaceutical composition according to claim 5 wherein the carrier is selected from among lactose, sucrose, starch, glucose, cellulose, methyl cellulose, magnesium stearate, lauryl sulfate, talc, vegetable oils, octyldecyl triglyceride, sodium bicarbonate, polysolvate, polyethylene glycol and lecithin.

9. A pharmaceutical composition according to claim 5 which contains 10 to 55% by weight of the active ingredient and is administered orally.

10. A pharmaceutical composition according to claim 5 which contains 1 to 20% by weight of the active ingredient and is administered parenterally.

11. A pharmaceutical composition according to claim 5 which is administered orally in a dose of 30 to 3000 mg/kg-body/day.

12. A pharmaceutical composition according to claim 5 which is an injection that is administered parenterally in a dose of 5 to 1000 mg/kg-body/day.

13. A pharmaceutical composition according to claim 5 which is a suppository that is administered in a dose of 5 to 1000 mg/kg-body/day.

14. A pharmaceutical composition according to claim 5 which is used to improved lipid metabolism.

15. An anti-tumor composition having activity against transplantable leukemia L-1210 which originated from spontaneous leukemia in DBA/2 mice and against Ehrlich, S-180, Meth A, L-121 and P-388 tumors, comprising an ascochlorin derivative of the formula

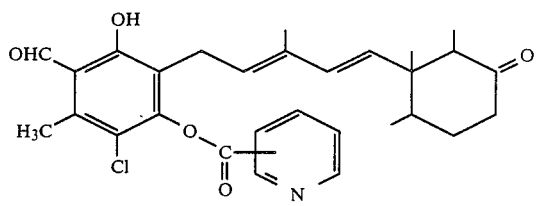

in an amount effective to treat a said tumor, and a pharmaceutically acceptable carrier.

* * * * *